United States Patent
Xu et al.

(10) Patent No.: US 7,108,771 B2
(45) Date of Patent: Sep. 19, 2006

(54) METHOD FOR REMOVAL OF IMPURITIES IN CYCLIC SILOXANES USEFUL AS PRECURSORS FOR LOW DIELECTRIC CONSTANT THIN FILMS

(75) Inventors: Chongying Xu, New Milford, CT (US); Thomas H. Baum, New Fairfield, CT (US); Alexander S. Borovik, Hartford, CT (US); Ziyun Wang, New Milford, CT (US); James T. Y. Lin, Austin, TX (US); Scott Battle, Cedar Park, TX (US); Ravi K. Laxman, San Jose, CA (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 10/015,326

(22) Filed: Dec. 13, 2001

(65) Prior Publication Data

US 2003/0116421 A1    Jun. 26, 2003

(51) Int. Cl.
*B01D 15/00* (2006.01)
*C07C 51/44* (2006.01)
*C02F 7/08* (2006.01)
*C02F 7/20* (2006.01)

(52) U.S. Cl. .................. 203/41; 203/14; 210/664; 528/10; 556/466

(58) Field of Classification Search .............. 203/68, 203/69, 70, 63, 64, 60, 41, 8, 14; 536/456, 536/450, 453; 556/460, 450, 451, 453, 464, 556/456, 466; 210/664; 528/10; 427/255.28; 438/680

See application file for complete search history.

(56) References Cited

U.S. PATENT DOCUMENTS

| | | | |
|---|---|---|---|
| 4,087,448 A * | 5/1978 | Rossmy et al. ............. 556/428 |
| 4,127,598 A * | 11/1978 | McEntee ..................... 556/442 |
| 4,156,689 A | 5/1979 | Ashby et al. |
| 4,374,110 A | 2/1983 | Darnell et al. |
| 4,670,299 A | 6/1987 | Fukuyama et al. |
| 4,745,169 A | 5/1988 | Sugiyama et al. |
| 4,755,370 A | 7/1988 | Kray et al. |
| 4,764,631 A * | 8/1988 | Halm et al. ................. 556/460 |
| 4,871,616 A | 10/1989 | Kimura et al. |
| 5,043,789 A | 8/1991 | Linde et al. |
| 5,047,492 A | 9/1991 | Weidner et al. |
| 5,098,865 A * | 3/1992 | Machado et al. ........... 438/788 |
| 5,204,134 A | 4/1993 | Girsh |

(Continued)

FOREIGN PATENT DOCUMENTS

| EP | 0543665 | * | 5/1993 |
| JP | 50-111198 | | 1/1974 |

OTHER PUBLICATIONS

Alfred Grill, et al., Novel Low-k Dual-Phase Materials Prepared by PECVD, Mat. Res. Soc. Symp. Proc. vol. 612, 2000 Materials Research Society.

(Continued)

*Primary Examiner*—Virginia Manoharan
(74) *Attorney, Agent, or Firm*—Steven J. Hultquist; Intellectual Property / Technology Law; Margaret Chappuis

(57) ABSTRACT

A process for reducing the level(s) of water and/or other impurities from cyclosiloxanes by either azeotropic distillation, or by contacting the cyclosiloxane compositions with an adsorbent bed material. The purified cyclosiloxane material is useful for forming low-dielectric constant thin films having dielectric constants of less than 3.0, more preferably 2.8 to 2.0.

17 Claims, 2 Drawing Sheets

U.S. PATENT DOCUMENTS

| | | |
|---|---|---|
| 5,210,250 A | 5/1993 | Watanuki et al. |
| 5,276,173 A * | 1/1994 | Marko et al. ............... 556/459 |
| 5,312,947 A * | 5/1994 | Tsukuno et al. ............ 556/456 |
| 5,484,867 A | 1/1996 | Lichtenhan et al. |
| 5,536,323 A | 7/1996 | Kirlin et al. |
| 5,711,816 A | 1/1998 | Kirlin et al. |
| 5,804,040 A | 9/1998 | Asai et al. |
| 5,879,649 A * | 3/1999 | Henderson et al. ......... 423/337 |
| 6,114,500 A | 9/2000 | Mori et al. |
| 6,171,945 B1 | 1/2001 | Mandal et al. |
| 6,368,359 B1 * | 4/2002 | Perry et al. .................... 8/142 |
| 6,383,955 B1 | 5/2002 | Matsuki et al. |
| 6,410,463 B1 | 6/2002 | Matsuki |
| 6,858,697 B1 | 2/2005 | Mayorga et al. |
| 2004/0054114 A1 | 3/2004 | Mayorga et al. |

OTHER PUBLICATIONS

Albert Wang, et al. "TMCTS for Gate Dielectric in Thin Film Transistors", Mat. Res. Soc. Meeting 1996.

A. Grill, et al., "Ultralow-k Dielectrics Prepared by Plasma-enhanced Chemical Vapor Deposition", Applied Physics Letters, vol. 79, No. 6, Aug. 6, 2001.

Mantz, et al., "Thermolysis of Polyhedral Oligomeric Silsesquioxane (POSS) Macromers and POSS-Siloxane Copolymers", Chem. Mater., 1996, 8, p. 1250-1259.

Ravi K. Laxman, Neil Hendrix Barry Arkles, Terry A. Tabler "Synthesizing Low-K CVD Materials for Fab Use" Semiconductor International, Nov. 1, 2000.

* cited by examiner

METHOD FOR REMOVAL OF IMPURITIES IN CYCLIC SILOXANES USEFUL AS PRECURSORS FOR LOW DIELECTRIC CONSTANT THIN FILMS

TECHNICAL FIELD OF THE INVENTION

The present invention relates generally to a method for purifying siloxanes, particularly, cyclic siloxanes, such as tetramethylcyclotetrasiloxane (TMCTS) useful as precursors to low dielectric constant thin films, as well as to a method for deposition of low dielectric constant thin films from a purified siloxane or cyclic siloxane precursor.

BACKGROUND OF THE INVENTION

As the need for integrated circuits for semiconductor devices having higher performance and greater functionality increases, device feature geometries continue to decrease. As device geometries become smaller, the dielectric constant of an insulating material used between conducting paths becomes an increasingly important factor in device performance.

As device dimensions shrink to less than 0.25 µm, propagation delay, cross-talk noise and power dissipation due to resistance-capacitance (RC) coupling become significant due to increased wiring capacitance, especially interline capacitance between the metal lines on the same level. These factors all depend critically on the dielectric constant of the separating insulator or inter-layer dielectric (ILD).

The use of low dielectric constant (k) materials advantageously lowers power consumption, reduces cross talk, and shortens signal delay for closely spaced conductors through the reduction of both nodal and interconnect line capacitances. Dielectric materials that exhibit low dielectric constants are critical in the development path toward faster and more power efficient microelectronics.

Alkyl silanes, alkoxy silanes and polyhedral oligomeric silsesquioxanes (POSS) and other materials comprised mainly of Si, C, O and H (SiCOH) are being evaluated aggressively for obtaining low dielectric constant (k) thin-films as interlayer dielectrics in an integrated circuit by a PECVD approach. The resulting films formed when using these precursors give dense SiCOH containing films, having dielectric constants in the range of from about 2.4 to 3.2.

Introducing porosity to the low-dielectric constant SiCOH films may serve to further lower the dielectric constant to values below 2.5.

One particular class of precursors, cyclosiloxanes, (i.e. 2,4,6,8-tetramethylcyclotetrasiloxane (TMCTS)) is being considered as a source material for the deposition of low dielectric constant (k) thin-films used as interlayer dielectrics in an integrated circuit. Cyclosiloxanes provide a thin film having an open crystal structures or cage structure (e.g. Mantz et al., "Thermolysis of Polyhedral Oligomeric Silsesquioxane (POSS) Macromers and POSS-Siloxane Copolymers", Chem. Mater., 1996, 8, 1250–1259). PECVD of thin films from such precursors results in open areas in the structure, which leads to low packing density and hence low k values.

Chemical vapor deposition (CVD) is the thin film deposition method of choice for large-scale fabrication of microelectronic device structures, and the semiconductor manufacturing industry has extensive expertise in its use.

The purification and reproducible delivery of cyclosiloxanes for CVD is extremely critical for full-scale commercialization of the thin-film process. At present the PECVD deposition process is suffering from irreproducible delivery due to polymerization of TMCTS within the delivery lines and process hardware. Questions related to the purification of TMCTS and elimination of the polymerization must be considered. The exact polymerization mechanism is presently not known. However, studies by the inventors of the instant invention indicate that catalytic polymerization of siloxanes occurs in the presence of water/moisture, Lewis acids and Lewis bases. Accordingly, there is a need in the art to reduce water content as well as other catalytic species from siloxanes, providing improved purity, stability and utility.

There are several synthetic routes to TMCTS. For example, Takiguchi et al., report in Japanese Unexamined Patent Publication (Kokai) 50-111198, that methyl cyclic siloxanes are produced by a process in which methyl trichlorosilane reacts mildly with water.

In a still further reference (Ravi K. Laxman, Neil H. Hendricks, Barry Arkles, Terry A. Tabler "Synthesizing Low-K CVD Materials for Fab Use" *Semiconductor International*, Nov. 1, 2000.) TMCTS is prepared through hydrolysis of methyldichlorosilane to firstly form a linear siloxane polymer that is end-capped with trimethylsilyl groups. Alternate synthetic procedures that avoid halogenated starting materials are anticipated.

Common impurities in TMCTS and other cyclosiloxanes include water and partially halogenated or chlorinated silicon species, which could potentially form acid species in the presence of moisture. The presence of water molecules and/or acidic impurities may result in acid catalyzed polymerization mechanisms of the cyclosiloxane materials.

Accordingly, it is desired to have the appropriate cyclosiloxane material as free as possible from impurities, because, if the cyclosiloxane material contains impurities, premature polymerization in the delivery lines is possible and causes the material to no longer be considered a valid candidate for VLSI applications.

Therefore, it is an objective of the present invention to purify cyclosiloxane materials for use as CVD precursors for low dielectric constant thin films.

It is a further objective of the present invention to reduce the levels of water, basic and/or acidic catalyst molecules in a cyclosiloxane material so as to prevent or minimize premature polymerization It is a further objective of the present invention to reduce the levels of water basic and/or acidic catalyst molecules in a cyclosiloxane material so as to prevent or minimize premature, impurity-catalyzed polymerization in a CVD reactor and associated delivery lines.

It is a still further object of the present invention to prepare low dielectric constant thin films from a cyclosiloxane precursor having reduced levels of water, basic and/or acidic impurities.

SUMMARY OF THE INVENTION

The present invention relates to the removal of water, basic and/or acidic impurities present in siloxanes and cyclosiloxanes, in connection with the use of such materials as chemical reagents.

In one aspect, the invention relates to a process for purification of a cyclosiloxane, CVD precursor, comprising water and optionally at least one other impurity selected from basic and acidic impurities, wherein said process is selected from the group consisting of:

(1) contacting the cyclosiloxane material with an adsorbent bed material, so as to remove therefrom at least a portion of the water and optionally one other impurity, to produce a cyclosiloxane precursor having a reduced level of water and optionally one other impurity; and removing the purified cyclosiloxane precursor from the adsorbent bed material; and (2) distilling a starting mixture comprising at least water and at least one cyclosiloxane CVD precursor, in the presence of an azeotropic component, so as to form an azeotropic mixture with the water contained in said starting mixture; in order to produce (A) a distillate fraction comprising water and the azeotropic component and (B) a balance fraction comprising cyclosiloxane, whereby said balance fraction (B) is substantially reduced in water relative to the starting mixture; and (3) a combination of 1 and 2.

In a further aspect, the present invention relates to a CVD method of depositing a low dielectric constant thin film on a substrate from a cyclosiloxane precursor that has been purified by a method selected from the group consisting of:

(1) contacting a cyclosiloxane precursor comprising water and optionally at least one other impurity selected from basic and acidic impurities, with an adsorbent bed material, so as to remove therefrom at least a portion of the water and optionally a portion of the other impurity, to produce a purified cyclosiloxane precursor having a reduced level of water and optionally at least one other impurity; and removing the purified cyclosiloxane precursor from the adsorbent bed; and (2) distilling a starting mixture comprising at least water and at least one cyclosiloxane CVD precursor, in the presence of an azeotropic component, so as to form an azeotropic mixture with the water contained in said starting mixture; in order to produce (A) a distillate fraction comprising water and the azeotropic component and (B) a balance fraction comprising cyclosiloxane, whereby said balance fraction (B) is substantially reduced in water relative to the starting mixture; and (3) a combination of 1 and 2.

In a still further aspect, the present invention relates to cyclic siloxanes, such as, 1,3,5,7-tetramethylcyclotetrasiloxane (TMCTS), purified by a method selected from the group consisting of:

(1) contacting a cyclosiloxane precursor comprising water and optionally at least one other impurity selected from basic and acidic impurities with an adsorbent bed material, so as to remove therefrom at least a portion of the water and optionally a portion of the other impurity, to produce a purified cyclosiloxane precursor having a reduced level of water and optionally at least one other impurity; and removing the purified cyclosiloxane precursor from the adsorbent bed; and (2) distilling a starting mixture comprising at least water and at least one cyclosiloxane CVD precursor, in the presence of an azeotropic component, so as to form an azeotropic mixture with the water contained in said starting mixture; in order to produce (A) a distillate fraction comprising water and the azeotropic component and (B) a balance fraction comprising cyclosiloxane, whereby said balance fraction (B) is substantially reduced in water relative to the starting mixture; and (3) a combination of 1 and 2.

Other aspects, features and embodiments of the invention will be more fully apparent from the ensuing disclosure and appended claims.

DETAILED DESCRIPTION OF THE INVENTION AND PREFERRED EMBODIMENTS THEREOF

Figure 1:
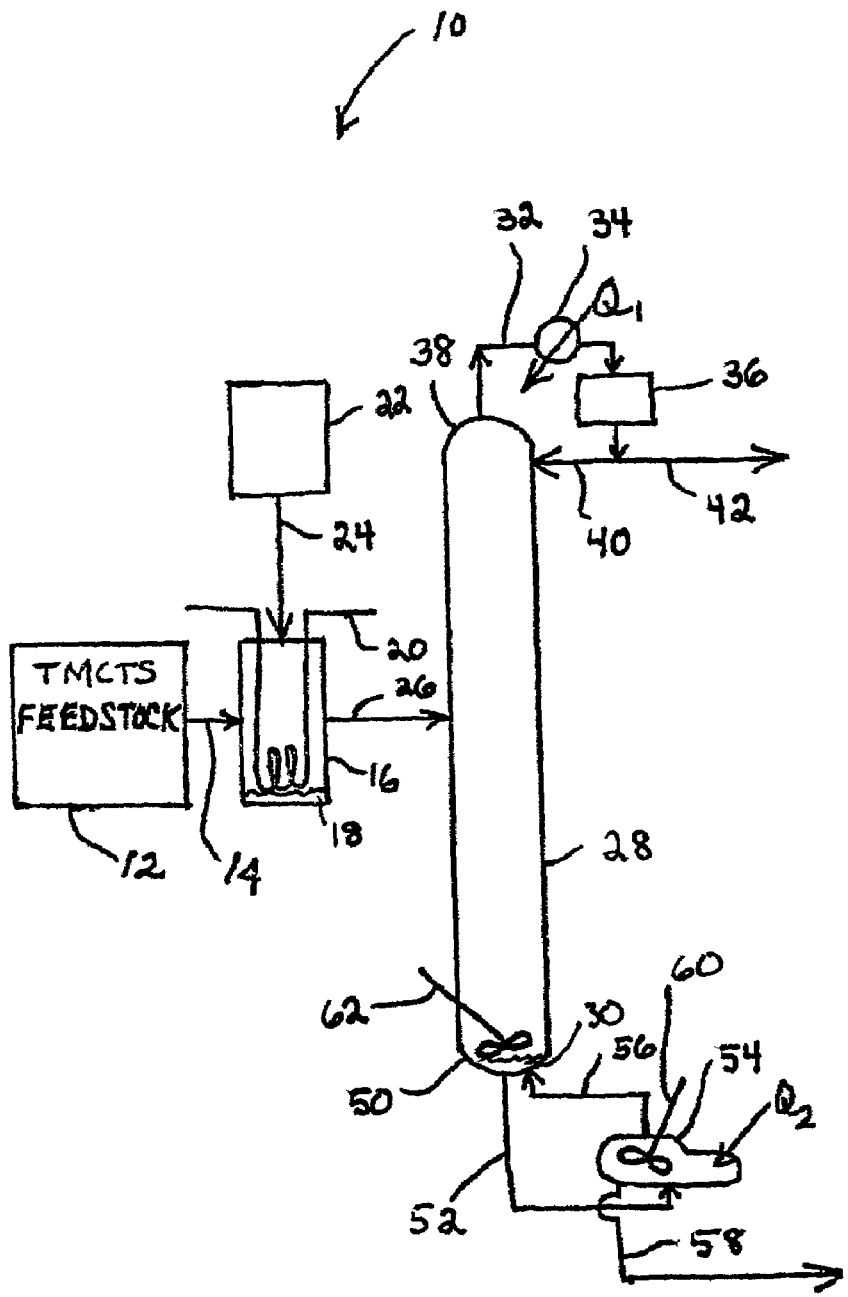
FIG. 1 shows a process flow sheet in accordance with one embodiment of the present invention.

Although described hereinafter primarily in reference to specific cyclosiloxanes, it will be appreciated that the method of the invention is not thus limited, but rather is broadly applicable to the purification and analysis of other siloxane materials, as well as mixtures of the foregoing. The ensuing discussion relating to cyclosiloxanes should therefore be understood to encompass such other silane materials, as variant feedstocks to which the purification methodology of the invention is usefully applied.

The present invention provides a method for obtaining purity levels of cyclosiloxane precursors, suitable for semiconductor device manufacturing applications, in which the cyclosiloxane precursor is useful for producing porous, low-dielectric constant, SiO and SiCOH thin films of correspondingly high purity.

As used herein: the term "low-dielectric constant" refers to a dielectric material with a value of the dielectric constant, k, below 3.0 as measured at a frequency of 1 mega-Hertz; the term "thin film" refers to a film having a thickness in the range of from about 1000 Å to about 2 μm; the term "SiO" refers to a thin film composition comprising from about 1 to about 40 atomic percent silicon, preferably from about 20 to 40 percent silicon and from about 1 to about 60 atomic percent oxygen, preferably from about 40 to 60 percent oxygen; and the term "SiCOH" refers to a thin film composition comprising from about 1 to about 40 atomic percent silicon, preferably from about 20 to 40 percent silicon, from about 1 to about 60 atomic percent oxygen, preferably from about 40 to 60 percent oxygen, from about 1 to about 50 atomic percent carbon, preferably from 5 to 17 percent carbon, from about 1 to 60 atomic percent hydrogen, and preferably from about 1 to 50 percent hydrogen.

The purification reagent compositions useful in the practice of the instant invention may alternatively comprise, consist of, or consist essentially of any of the purification components hereinafter described, and such compositions may additionally, or alternatively, exclude or be substantially free of any components not specifically described herein as being included or includable in such compositions.

In one embodiment, the invention relates to a process for reducing the concentration of water and optionally at least one other impurity, from a cyclosiloxane precursor material, (e.g., to levels<10 ppm), wherein the other impurity is selected from the group consisting of acidic and basic impurities.

Chlorosilanes are typically the building blocks of cyclosiloxanes as shown in formula (1) below:

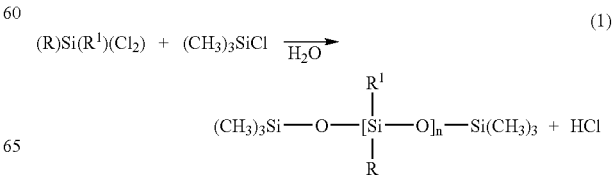

The product is a linear siloxane polymer having n number of repeating units. The linear siloxane polymer is subsequently "backcracked" to form a combination of cyclosiloxanes, predominantly 6-, 8- and 10-membered rings (formula 2):

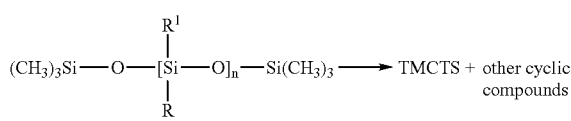

(2)

The combination of cyclosiloxanes is fractionally distilled to isolate the various cyclic compounds. While distillation is useful in removing certain impurities, it is relatively inefficient in removing trace amounts of water and certain basic and/or acidic impurities, to levels sufficient to prevent premature polymerization of the cyclosiloxane precursors and hence for use in CVD of low dielectric constant thin films in device manufacturing of integrated circuits.

In the CVD process, a precursor is delivered to a CVD reactor in vapor form. In the case of solids and liquids, this requires heating of the delivery lines, CVD chamber and substrate. It is speculated that, cyclosiloxanes, particularly TMCTS, prematurely polymerize in the heated delivery lines due to the presence of trace water and/or other trace impurities such as acidic or basic impurities, in the bulk cyclosiloxane material, through a ring opening mechanism. The water and/or other impurities most probably originate from the synthetic process used to produce the cyclosiloxanes, as described hereinabove.

The present invention is useful for removing water to levels in the range of from about 1 to 20 ppm and acidic impurities to levels in the range of from about 0.001 to 0.00001%.

In one embodiment, the invention relates to a process for reducing the concentration of water and optionally at least one other impurity selected from acidic and basic impurities, from a cyclosiloxane precursor, wherein said process is selected from the group consisting of:

(1) contacting the cyclosiloxane precursor with an adsorbent bed material, so as to remove therefrom at least a portion of the water, and optionally at least one other impurity, to produce a cyclosiloxane precursor having a reduced level of water and optionally at least one other impurity; and removing the purified cyclosiloxane precursor from the adsorbent bed material; and (2) distilling a starting mixture comprising at least water and at least one cyclosiloxane CVD precursor, in the presence of an azeotropic component, so as to form an azeotropic mixture with the water contained in said starting mixture; in order to produce (A) a distillate fraction comprising water and the azeotropic component and (B) a balance fraction comprising cyclosiloxane, whereby said balance fraction (B) is substantially reduced in water relative to said starting mixture; and (3) a combination of 1 and 2.

In one embodiment, the cyclosiloxane to be purified comprises the formula $[R\ R'Si—O]_n$ wherein each of R and R' is same or different and independently selected from the group consisting of hydrogen, $C_1$–$C_8$ alkyl, $C_1$–$C_8$ alkoxy, $C_1$–$C_8$ alkene, $C_1$–$C_8$ alkyne, and $C_1$–$C_8$ carboxyl; and n is from 2 to 8. In a preferred embodiment, the cyclosiloxane is selected from the group consisting of: polyhedral oligomeric silsesquioxanes (POSS), octamethylcyclotetrasiloxane (OMCTS), more specifically 1,1,3,3,5,5,7,7-octamethylcyclotetrasiloxane (OMCTS), hexamethylcyclotetra-siloxane (HMCTS), more specifically 1,1,3,5,5,7-hexamethylcyclotetrasiloxane (HMCTS), tetramethylcyclotetrasiloxane (TMCTS), more specifically 1,3,5,7-tetramethylcyclotetrasiloxane (TMCTS), and mixtures thereof. In the most preferred embodiment, the cyclosiloxane to be purified is 1,3,5,7-tetramethylcyclotetrasiloxane (TMCTS).

In one embodiment, the present invention relates to a process for purification of at least one cyclosiloxane precursor comprising at least water and optionally at least one other impurity selected from acidic and basic impurities, said cyclosioxane comprising the formula $[R\ R'\ Si—O]_n$, wherein each of R and $R^1$ is same or different and independently selected from the group consisting of hydrogen, $C_1$–$C_8$ alkyl, $C_1$–$C_8$ alkoxy, $C_1$–$C_8$ alkene, $C_1$–$C_8$ alkyne, and $C_1$–$C_8$ carboxyl; and n is from 2 to 8, said process comprising contacting the cyclosiloxane material with an adsorbent bed material, so as to remove at least a portion of the water and optionally a portion of the acidic and/or basic impurity therefrom.

As used herein an adsorbent or drying agent is defined as a substance that absorbs water and/or other impurities. Drying agents or adsorbents are grouped into two major classes: chemically acting and physically acting drying agents.

Chemically acting drying agents are substances that bind water in the form of crystallization and may be regenerated by warming. Examples of these types of drying agents are calcium chloride, sodium sulfate, or magnesium sulfate. The second subdivision of chemically acting drying agents is substances that react with water. Regeneration of these drying agents is not possible since the drying agent has undergone a chemical change. Examples of these types of drying agents are, phosphorus pentoxide, metals, and metal hydrides, such as calcium hydride.

Physically acting drying agents are substances that adsorb water and or other impurities on the surface and in the pores of the drying agent. These drying agents can be regenerated by warming or applying a vacuum. Examples of these types of drying agents are, desiccant, silica gel, molecular sieves, carbon and aluminum oxide.

The adsorbent bed material used in the purification process of the instant invention may comprise one of many adsorbents and/or drying agents and/or mixtures thereof, having affinity for water and/or at least one acidic impurity. Such adsorbents are readily known to those skilled in the art. For example, the adsorbent may comprise activated carbon adsorbent, (beads or powder), having an average particle size of from about 30 to 50 μm with a pore size distribution of from about 10 to 50 nm. Further, the adsorbent bed material may comprise molecular sieves, having a particle size distribution from about 100 to 125 μm and a pore size distribution from about 10 to 50 nm. Still further, the adsorbent bed material may comprise calcium hydride, or calcium oxide, etc. In a preferred embodiment, the adsorbent is selected from calcium oxide and calcium hydride.

In one embodiment, the adsorbent bed material may comprise a combination or series of adsorbents and/or drying agents. For example, the cyclosiloxane precursor may first contact a drying agent such as calcium hydride to adsorb water molecules and separately contact a carbon adsorbent material for adsorption of an acidic impurity. As a second example the adsorbent bed material may comprise a combination of both calcium hydride and carbon adsorbent to remove both water and acidic impurity in a single step.

The amount of adsorbent used is dependent on the concentration of water and optionally other impurities present in the cyclosiloxane precursor material to be purified and the capacity of the adsorbent bed material. In one embodiment, the adsorbent may be useful in reducing water levels to <20 ppm.

The adsorbent bed material may be placed in a distillation flask or in a separate column so long as the cyclosiloxane to be purified contacts the adsorbent bed material for a period of time sufficient to remove at least a portion of the impurity from the cyclosiloxane precursor. In one embodiment, the cyclosiloxane precursor contacts the adsorbent bed material from about 1 minute to about 10 hours, more preferably from about 30 minutes to 2 hours.

In one embodiment, a first volume of cyclosiloxane precursor to be purified is used to wet the adsorbent bed until the adsorbent bed is wet. A period of time is allowed to pass until the adsorbent material, which upon being wetted gives off heat, reaches room temperature. At that time the first volume of purified cyclosiloxane precursor is segregated and there is then continuously or intermittently passed into the adsorbent bed the cyclosiloxane precursor material to be purified. This particular purification step may be repeated as many times as necessary to reduce the selected impurity to within a desired specification range. When the adsorbent bed has been saturated with the impurities then the adsorbent material may be discarded or recycled for further use.

In one embodiment, the adsorbent bed material may be positioned in a distillation flask. The distillation flask may be of any size and or shape and the adsorbent should not exceed 20% and preferably 10% of the total volume. In one embodiment, the volume of the distillation flask is from 1 to 100 liters, preferably from 5 to 50 liters having a capacity of from about 2% to 20% adsorbent. In such an embodiment, the purified cyclosiloxane material may be removed from the adsorbent bed material by distillation.

In a further embodiment the adsorbent bed may be integrated in the form of a column The column. may for example have a volume in the range of from about 1 to 50 liters and preferably from 2 to 10 liters. The cyclosiloxane to be purified may be pumped or gravity fed through the column and into a flask. The adsorbent bed is most desirably incorporated in the form of a column through which the TMCTS can be pumped. An example of an adsorbent bed in a column, for instance is one in which the adsorbent bed has a cross-sectional area of from about 0.1 to 20 inches and preferably from 0.5 to 4, and about 1 of 10% molecular sieves. The above data on a typical adsorbent bed is not given for any purpose of limiting the instant invention, it is given for the purpose of illustrating a typical bed of adsorbent molecular sieves that can be utilized within the scope of the instant invention. The TMCTS then is pumped or gravity fed through the adsorbent bed to obtain a product having a reduced level of acidic and/or basic impurity or water. Generally, the adsorbent process is preferably carried out anywhere at a temperature of from about 0° C. to 35° C. It is undesirable to carry out the adsorbent process at a temperature of the adsorbent bed above 35° C., since the adsorption may not be as efficient at that point. Further, the acidic and/or basic impurities may tend to vaporize at temperatures above that level. With respect to the 0° C. lower limit, the only reason the lower limit appears is that it is difficult to refrigerate an adsorbent bed below the 0° C. level. However, temperatures below 0° C. for the adsorbent bed could be utilized to carty out the adsorption process therewith. Preferably, the adsorption process is carried out at room temperature since this does not require refrigeration. It should be pointed out that before the TMCTS is passed through the adsorbent bed, it is desirable that the TMCTS be purified as much as possible by distillation so that the impurities easily separated by distillation are not present in the TMCTS stream and thus become adsorbed on the adsorbent bed, saturating it with impurities, thus, shortening its useful life. Accordingly, it is highly desirable that the TMCTS before it is passed through the adsorbent bed, be purified by distillation once, twice or more times before it is subjected to the instant process. The residence time of the stream of TMCTS in the adsorbent bed will vary with practice. It has been found that a residence time of as little as 0.5 hours in the adsorbent bed will remove a substantial amount of water and/or basic and/or acidic impurities while a maximum time of 10 hours will more completely purify the stream of TMCTS.

Preferably, the adsorption process is carried out at room temperature. However, any temperature below the boiling point of any single component in the cyclosiloxane material to be purified is sufficient.

The adsorption, purification step of the instant invention may be carried out in combination with a series of additional purification steps or processes. For example, the cyclosiloxane to be purified may be filtered, distilled, extracted, etc. prior to or subsequent to contacting the adsorbent bed material.

The purified cyclosiloxane precursor is isolated from the adsorbent material by any method readily known to those skilled in the art. Preferably the method of isolation used is selected from decantation, distillation and pump. More preferably, the purified cyclosiloxane is distilled.

In one embodiment, the impurities present in TMCTS produced for microelectronics fabrication applications comprise the formula $(R)_aSi(X)_b$ wherein R is selected from the group consisting of H, and $C_1$ to $C_4$, X is halogen, a is from 0 to 3 and b is from 1 to 4. The method of the present invention enables impurity levels to be reduced to levels <0.001% and more preferably to <0.00001% in the purified TMCTS product.

In a further embodiment, the present invention relates to a process for reducing the concentration of water in at least one cyclosiloxane precursor comprising at least water and optionally at least one other impurity selected from acidic and basic impurities, said cyclosiloxane comprising the formula $[R\ R'Si-O]_n$, wherein each of R and $R^1$ is same or different and independently selected from the group consisting of hydrogen, $C_1$–$C_8$ alkyl, $C_1$–$C_8$ alkoxy, $C_1$–$C_8$ alkene, $C_1$–$C_8$ alkyne, and $C_1$–$C_8$ carboxyl; and n is from 2 to 8, said process comprising distilling a starting mixture comprising at least water and at least one cyclosiloxane precursor in the presence of at least one azeotropic component selected from the group consisting of: benzene, ethanol, 2-propanol, butyl acetate, phenol, chloroform, methyl acrylate, isopropyl formate, isopropyl acetate, cyclohexane, and n-heptane, so as to form an azeotropic mixture with the water contained in said starting mixture; in order to produce (A) a distillate fraction comprising water and the azeotropic component and (B) a balance fraction comprising cyclic siloxane, whereby said balance fraction (B) is substantially reduced in water relative to the starting mixture.

As used herein, the term "azeotrope" is defined as a constant boiling mixture, having a fixed composition, which cannot be altered by normal distillation.

The azeotropic component employed in the invention should form an azeotrope with water. Examples of azeotropic components as well as the azeotrope boiling point, include but are not limited to:

| Azeotropic Component | Boiling Point (° C.) |
| --- | --- |
| Ethanol | 78.17 |
| Benzene | 69.4 |
| 2-propanol | 80.4 |
| Butyl acetate | 90.7 |
| Phenol | 99.5 |
| Chloroform | 56.1 |
| Methyl acrylate | 71.0 |
| Isopropyl formate | 65.0 |
| Isopropyl acetate | 76.6 |
| Cyclohexane | 69.5 |
| n-heptane | 79.2 |
| Di-iso-propyl ether | 62.2 |
| toluene | 84.1 |

The azeotropic components employed in the invention form azeotropes with water having boiling points that are sufficiently different from the boiling points of the cyclosiloxane. In a preferred embodiment, the cyclosiloxane precursor to be purified is TMCTS (boiling point=135° C.) and the azeotropic component is benzene.

In one embodiment, the azeotropic component forms an azeotrope with water, wherein the azeotrope has a boiling point that is at least 10° C. less than the cyclosiloxane precursor being purified, more preferably at least 30° C., and most preferably at least 50° C. below the boiling point of the cyclic siloxane precursor to be purified. A particularly preferred azeotropic component useful in the present invention is benzene, which forms an azeotrope with water at 69.4° C.

By virtue of its low boiling point in relation to TMCTS, the water/benzene azeotrope is readily removed by distillation from the TMCTS, to yield a cyclic siloxane having water levels in the range of from about 1 to 50 ppm, more preferably in a range of from 1 to 20 ppm and most preferably in a range of from 1 to 10 ppm.

In a further embodiment, the invention relates to a process for reducing the concentration of water and at least one other impurity selected from the group consisting of acidic and basic impurities, in a cyclosiloxane precursor, comprising:

(1) contacting the cyclosiloxane precursor with an adsorbent bed material, so as to remove therefrom at least a portion of the impurity, to produce a cyclosiloxane precursor having a reduced level of impurity;

(2) distilling the cyclosiloxane precursor having a reduced level of impurity in the presence of at least one azeotropic component so as to form an azeotropic mixture with the water contained in said starting mixture; in order to produce (A) a distillate fraction comprising water and the azeotropic component and (B) a balance fraction comprising cyclosiloxane, whereby said balance fraction (B) is substantially reduced in water relative to the starting mixture; and (3) distilling said balance fraction (B) to isolate cyclosiloxane precursor having reduced levels of impurity and water.

In one embodiment, the concentration of water in the original cyclosiloxane to be purified is measured by analytical methods known to those skilled in the art, including but not limited to: Karl Fisher titration, gas chromatography, Fourier Transform Infrared spectroscopy, etc. Such analysis provides for a more precise measurement as to the volume of the azeotropic component or adsorbent material necessary to remove the required portion of the water and/or acidic impurity.

Additionally, the wide separation of the boiling points of the azeotrope and cyclosiloxane precursor, permits the water fraction to be quantitatively recovered and assayed to determine the complete removal of required amounts of water and/or acidic impurity in the starting material. After quantitatively removing the impurities, conventional analytical methods such as Karl Fisher titration, GC-MS with chemical derivatization and ICP/MS may be used for further analysis of the purified cyclosiloxane precursor material. The invention thereby enables ultra-high purity (ppb) analyses of cyclosiloxanes and mixtures thereof, for semiconductor applications.

An illustrative process system for purification of water and impurity-containing TMCTS is schematically depicted in FIG. 1.

As illustrated, the process system (10) includes a vessel (12) containing TMCTS including water and at least one impurity species therein ("TMCTS FEEDSTOCK"), from which the water and impurity-containing TMCTS liquid is flowed in line (14) to chemical purification reactor (16) containing adsorbent bed material (18). The reactor 16 is equipped with heating means 20.

The heating means can be of any suitable type, with the illustrated element being a heat exchange passage through which a heating medium can be flowed, to heat the TMCTS feedstock in the vessel. Alternatively, the heating means can include a heating jacket, a resistance heating coil positioned in the interior liquid-holding volume of the vessel (16), a steam-tracing conduit or jacket on line 14, infrared heating lamps, etc.

The heating means (20) is an optional feature since as mentioned the reaction of the adsorbent bed material and the TMCTS feedstock may be carried out at ambient temperature, but heating of the reaction medium affords the advantage of faster reaction rates and smaller vessel size, as compared to ambient temperature reaction.

The adsorbent is provided from a source vessel (22) and may be flowed to the reaction vessel (16) via line (24), or alternatively dosed into the liquid reaction volume via an automatic dose metering system (not shown in FIG. 1).

The reaction of the adsorbent bed material with the water and at least one other impurity serves to adsorb at least a portion of the impurity and or water. For example, the TMCTS feedstock may illustratively contain 550 parts per million of acidic impurity and/or 550 parts per million water. The adsorbent bed material adsorbs thereon at least a portion of the acidic impurity and optionally at least a portion of the water, to produce a TMCTS precursor material having reduced levels of acidic impurity and/or water. Next, the TMCTS precursor material, having a reduced level of at least acidic impurity is transferred in line (26) to the distillation column (28) containing an azeotropic component, benzene (38). The distillation column (28) is of conventional construction and has at its overhead portion (30) a total overhead condenser assembly comprising condenser (34) and condensate tank (36) through which overhead flows in line (32). The benzene reacts with the water in the TMCTS precursor material to produce a benzene/water azeotrope that is easily separated from the distilling TMCTS. The benzene desirably is added in stoichiometric excess to ensure maximal removal of the water in the TMCTS feedstock. The reaction volume in this illustrative embodiment will then include at least TMCTS, water/benzene, azeotrope and excess benzene.

The volumetric flow rate of TMCTS feedstock to the vessel (16) can be controlled by flow control means, e.g., mass flow controllers, automatic flow control valves, etc., to provide a desired residence time of the TMCTS feedstock in the vessel for substantially complete reaction.

The overhead vapor is flowed in line (32) to the condenser (36) in which cooling water or other heat exchange medium is flowed to extract heat (enthalpy $Q_1$) of vaporization and effect condensation of the vapor. The vapor then flows into condensate tank (36) from which a portion is recycled as reflux in line (40) to the overhead portion of the column, and a portion is flowed in line (42) out of the system. A first fraction comprising the benzene/water azeotrope, a second fraction comprising excess benzene and a third fraction comprising high purity TMCTS having greatly reduced levels of water, (e.g., having <10 parts per billion water impurity) are isolated.

At the bottom portion (50) of the column (28), bottoms liquid is withdrawn in line (52) and flowed to the reboiler (54) in which the bottoms liquid is partially revaporized by heat input $Q_2$. Resultant reboil vapor is flowed in line (56) back into the lower portion (50) of the column. The bottom product liquid is withdrawn from the reboiler (54) in line (58) and flows to waste or is recycled for further distillation.

The lower portion (50) of the column (28) optionally may have disposed therein an agitator or mixer element (52) to ensure azeotropic component/water contact, particularly if the azeotropic component is introduced directly into the column or into feed line (26) as hereafter described. For the same reason, reboiler (54) optionally may have a corresponding agitator or mixer element (60) therein, to effect a suitable level of azeotropic component/water contact.

The boiling points of the respective components of the liquid flowed to the first column (28) are as follows: TMCTS=134° C.; benzene/water azeotrope=69.4° C.; and benzene 80° C. The substantial variance between the TMCTS, the benzene/water azeotrope and the benzene facilitates sharp and quantitative separations, and enables the production of ultra-high TMCTS.

As an alternative to the use of the reaction vessel (16) in the FIG. 1 system, such system can alternatively be operated within the distillation flask (28), thereby obviating the need for any reaction vessel upstream of the column.

Further, although the FIG. 1 embodiment is shown and described as a continuous flow system, it will be appreciated that the system may be constructed and arranged for batch or semi-batch operation, within the broad scope of the present invention.

In a further aspect, the present invention relates to a CVD method of depositing a low dielectric constant thin film on a substrate from a cyclosiloxane precursor that has been purified by a method selected from the group consisting of:

(1) contacting a cyclosiloxane precursor comprising water and optionally at least one impurity selected from the group consisting of acidic and basic impurities, with an adsorbent bed material, so as to remove therefrom at least a portion of the water and optionally a portion of the impurity, to produce a purified cyclosiloxane precursor having a reduced level of water and optionally impurity; and removing the purified cyclosiloxane precursor from the adsorbent bed; and (2) distilling a starting mixture comprising at least water and at least one cyclosiloxane CVD precursor, in the presence of an azeotropic component, so as to form an azeotropic mixture with the water contained in said starting mixture; in order to produce (A) a distillate fraction comprising water and the azeotropic component and (B) a balance fraction comprising purified cyclosiloxane precursor, whereby said balance fraction (B) is substantially reduced in water relative to the starting mixture; and (3) a combination of 1 and 2;

wherein said CVD method comprises the steps of:

placing the substrate in a chemical vapor deposition apparatus;

introducing at least one vaporized organosilicon precursor comprising the purified cyclosiloxane precursor into the apparatus;

transporting the purified cyclosiloxane precursor vapor into a chemical vapor deposition zone containing a substrate, optionally using a carrier gas to effect such transport;

contacting the purified cyclosiloxane precursor vapor with the substrate under chemical vapor deposition conditions to deposit a thin film comprising an organosilicon composition; and annealing the organosilicon thin film to produce a porous, SiCOH, low dielectric constant thin film.

In a further embodiment purified cyclosiloxane precursor vapor comprising from about 1 to about 100% by volume of a cyclosiloxane precursor, from about 0 to about 99% by volume of an inert carrier gas, and from about 1 to about 99% by volume of at least one co-reactant, based on the total volume of the purified cyclosiloxane precursor vapor, inert carrier gas and co-reactant, is subjected to chemical vapor deposition (CVD) conditions, preferably plasma enhanced chemical vapor deposition conditions in a plasma chamber containing a substrate, so that the precursor composition in vapor or plasma form is contacted with the substrate in the CVD chamber to deposit thereon, a dense SiCOH thin film.

For the purpose of depositing the SiCOH thin films of the present invention, the cyclosiloxane precursors may optionally be used in combination with other co-reactants. The co-reactant may comprise a liquid and/or gas and may comprise organic and/or organosilicon precursors. Preferred co-reactants may be selected from one or more of, $C_1$–$C_8$ alkyl, $C_1$–$C_8$ alkoxy, $C_1$–$C_8$ alkene, $C_1$–$C_8$ alkyne, $C_1$–$C_8$ aryl, $C_5C_{12}$ aryl and $C_1$–$C_8$ carboxyl, reactive gases and mixtures thereof. The reactive gases may include one or more of $CO_2$, ethylene, acetylene, $N_2O$, $O_2$, $H_2$ and mixtures thereof.

The inert carrier gas in the processes described hereinabove may be of any suitable type, (e.g., argon, helium, etc.), or a compressible gas or liquid, (e.g., $CO_2$).

In a preferred embodiment, the SiCOH thin film is deposited from a purified cyclosiloxane precursor by plasma enhanced CVD (PECVD). The plasma may be generated from single or mixed frequency RF power. The plasma source may comprise a high frequency, radio frequency (HFRF) plasma source component generating power in a range of from about 75 W to about 200 W at a frequency of about 13.56 MHz or a low frequency radio frequency (LFRF) plasma source component generating power in a range from about 5 W and 75 W at a frequency of about 350 kHz and/or combinations thereof. The plasma is maintained for a period of time sufficient to deposit the dense SiCOH thin film having retained therein a degree of the cage like structure of the original cyclosiloxane precursor.

In a preferred embodiment, the PECVD process is tuned with single frequency or dual frequency operating simultaneously to yield a SiCOH thin film having retained therein between 1 and 50% and more preferably between 5% and 30% percent of the original cyclosiloxane cage like structure.

In a further embodiment, the SiCOH thin film is post annealed in a furnace, at a temperature in the range of from about 100° C. to about 400° C., optionally in the presence of an oxidizing or reducing gas. Optionally the SiCOH thin film may be annealed at a gradually increasing temperature profile. Preferably the SiCOH thin film is annealed at a temperature of about 400° C.

Specific CVD conditions and more particularly PECVD conditions are readily determinable for a given application by empirically varying the process conditions (e.g., pressure, temperature, flow rate, relative proportions of the cyclosiloxane precursor gas and inert carrier gas in the composition, etc.) and developing correlation to the film properties produced in the process. The conditions of the process as disclosed herein are monitored to retain the cage like structure in the dense SiCOH film.

Figure 2:
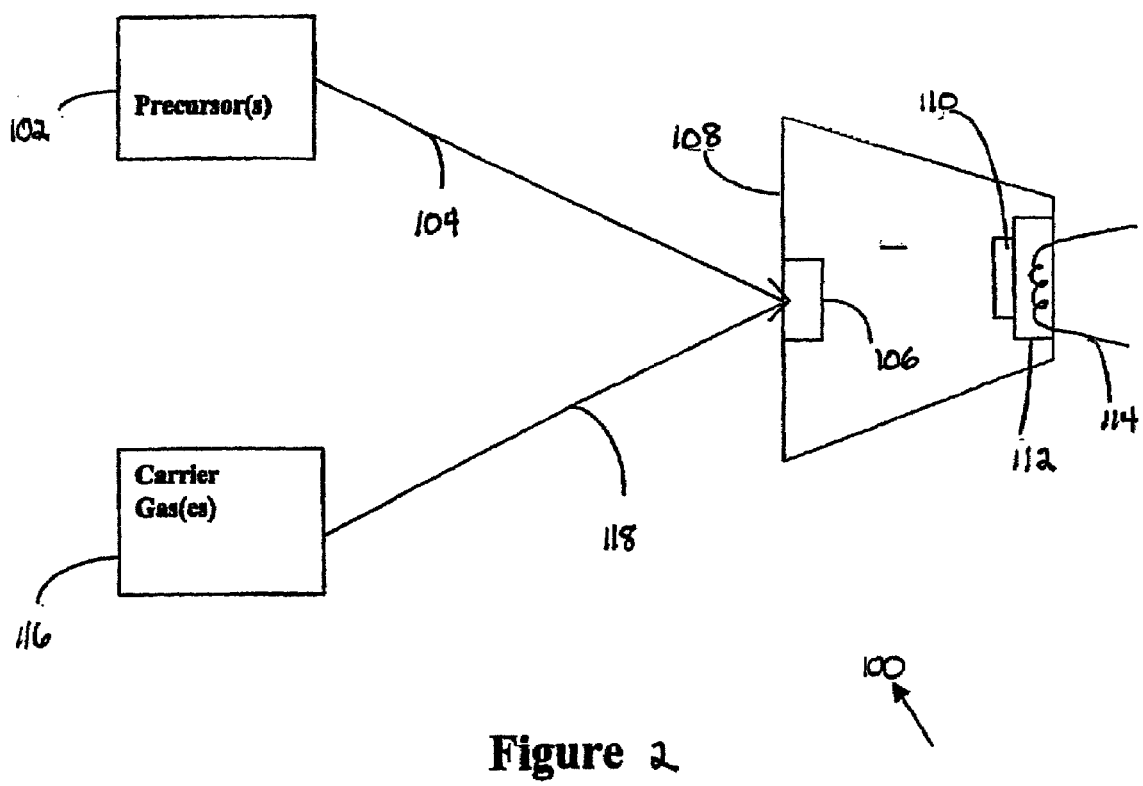
FIG. 2 is a schematic representation of a PECVD process system in accordance with one embodiment of the invention

FIG. 2 is a schematic representation of a process system (100) for forming a low k dielectric film on a substrate in accordance with one embodiment of the invention.

In process system (100), a source (102) of purified cyclosiloxane precursor(s) is joined by line (104) to disperser (i.e., showerhead or aerosol nozzle) (106) in CVD reactor (108). The CVD reactor may be constructed and arranged to carry out CVD involving thermal dissociation of the precursor vapor to deposit the desired SiCOH film on the substrate (110) mounted on susceptor (112) heated by heating element (114). Alternatively, the CVD reactor may be constructed and arranged for carrying out plasma-enhanced CVD, by ionization of the precursor gas mixture.

A source (116) of carrier gases is also provided, joined by line (118) to the disperser (106) in CVD reactor (108).

The disperser (106) may comprise a showerhead nozzle, jet or the like which functions to receive and mix the feed streams from the respective sources (102), and (116), to form a gaseous precursor mixture which then is flowed toward the substrate (110) on the heated susceptor (112). The substrate (110) may be a silicon wafer or other substrate element and material, on which the low k dielectric film is deposited.

In lieu of mixing the respective feed streams from lines (104) and (118) in the disperser, the streams may be combined in a mixing vessel or chamber upstream of the CVD reactor (108). Further, it will be appreciated that if the CVD reactor is configured and operated for carrying out PECVD, a plasma generator unit may be provided as part of or upstream of the CVD reactor (108).

The feed streams from sources (102) and (116) may be monitored in lines (104) and (118), respectively, by means of suitable monitoring devices (not shown in FIG. 2), and the flow rates of the respective streams may be independently controlled (by means such as mass flow controllers, pumps, blowers, flow control valves, regulators, restricted flow orifice elements, etc., also not shown) to provide a combined precursor feed stream having a desired compositional character.

The precursor formulations of the invention may be employed in any suitable chemical vapor deposition system to form corresponding thin films on a substrate or microelectronic device precursor structure as a dielectric layer thereon. The CVD system may for example comprise a liquid delivery CVD system, a bubbler-based CVD system, or a CVD system of any other suitable type. Suitable liquid delivery CVD systems include those disclosed in Kirlin et al. U.S. Pat. No. 5,204,134; Kirlin et al. U.S. Pat. No. 5,536,323; and Kirlin et al. U.S. Pat. No. 5,711,816.

In liquid delivery CVD, the source liquid may comprise the source reagent compound(s) or complex(es) per se, if the compound(s) or complex(es) are in the liquid phase at ambient temperature (e.g., room temperature, 25° C.) or otherwise at the supply temperature from which the source reagent is rapidly heated and vaporized to form precursor vapor for the CVD process. Alternatively, if the source reagent compound or complex is a solid at ambient or the supply temperature, such compound(s) or complex(es) can be dissolved or suspended in a compatible solvent medium to provide a liquid phase composition that can be submitted to rapid heating and vaporization to form precursor vapor for the CVD process. The precursor vapor resulting from the vaporization then is transported, optionally in combination with a carrier gas (e.g., He, Ar, $H_2$, $O_2$, etc.), to the chemical vapor deposition reactor where the vapor is contacted with a substrate at elevated temperature to deposit material from the vapor phase onto the substrate or semiconductor device precursor structure positioned in the CVD reactor.

In addition to flash vaporizer liquid delivery systems, other reagent delivery systems such as bubblers and heated vessels can be employed. In bubbler-based delivery systems, an inert carrier gas is bubbled through the precursor composition to provide a resulting fluid stream that is wholly or partially saturated with the vapor of the precursor composition, for flow to the CVD tool.

Accordingly, any method that delivers the precursor composition to the CVD tool may be usefully employed.

The PECVD method disclosed herein is an improvement over the prior art in that thin films are deposited from cyclosiloxane precursors having reduced levels of acidic impurities and water. By employing the purified cyclosiloxane PECVD precursors of the present invention the mean time to service of the CVD tool is reduced significantly and the reproducibility of the thin film process is improved.

Further, the low dielectric constant thin films produced by PECVD deposition of cyclosiloxanes purified by the method disclosed herein are of superb quality achieving dielectric constants between 3.0 and 2.0, more preferably between 2.8 and 2.2.

The features, aspects and advantages of the present invention are further shown with reference to the following non-limiting example relating to the invention.

EXAMPLES

Example 1

A 12L flask equipped with a condenser, was charged with 5,000 grams of 1,3,5,7-tetramethylcyclotetrasiloxane (TMCTS) and 50 grams of $CaH_2$ and a magnetic stir bar. The water content in the raw TMCTS was 125 ppm. The mixture was heated to reflux for about 10 hours with stirring under nitrogen protection. The condenser was then replaced by a distillation head and started to distill the TMCTS. After 170 g of fore-cuts was received, we collected 3470 grams of dry TMCTS. The water content in the dry TMCTS was analyzed to be below 5 ppm.

In a separate experiment, 100 grams of the raw TMCTS (with 125 ppm water) was mixed with 1% of $CaH_2$ at room temperature. The mixture was magnetically stirred. The water content in TMCTS was monitored over time by taken out aliquots of TMCTS from the flask for water analysis. After 20 min, 2 hour and 4 hour drying at room temperature, its water content dropped to 12 ppm, 6 ppm and 2 ppm, respectively.

Example 2

In a dry box, a 100 mL flask equipped with a condenser, was charged with 50 grams of raw TMCTS and 2 grams of anhydrous CaO and a magnetic stir bar. The water content in the TMCTS was 125 ppm. The flask was taken out of the box. Under nitrogen protection, the TMCTS was refluxed for 10 hours. Then dry TMCTS was distilled over CaO. The water content in the distilled TMCTS was analyzed to be below 10 ppm.

Example 3

Raw TMCTS with 125 ppm water was mixed with 10% an azeotropic reagent in a distillation flask. The water content in the raw TMCTS was 125 ppm. After 20% TMCTS was distilled out azeotropically, the dried TMCTS was collected. The water contents in the dried TMCTS with different azeotropic agents are listed below:

| Azeotropic agent | iso-Propyl alcohol | Di-iso-propyl ether | Toluene |
|---|---|---|---|
| Water content | <10 ppm | <20 ppm | 100 ppm |

Example 4

100 grams of raw TMCTS (with 125 ppm water) was mixed with 5 grams activated neutral molecular sieve at room temperature. After two days, an aliquot of TMCTS was taken and analyzed. Its water content was below 10 ppm.

Example 5

Raw TMCTS was mixed with 1% of $MgSO_4$ at room temperature. TMCTS became very viscous overnight. NMR study revealed the TMCTS was completely polymerized.

Although the invention has been variously disclosed herein with reference to illustrative aspects, embodiments and features, it will be appreciated that the aspects, embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. A process for improving delivery reproducibility of a cyclosiloxane precursor to a chemical vapor deposition reactor and reducing water content in the cyclosiloxane precursor, the process comprising the steps of:
   (a) providing a cyclosiloxane precursor;
   (b) treating and contacting the cyclosiloxane precursor with at least one adsorbent bed material that has an affinity for water and at least one impurity selected from the group consisting of acidic and basic impurities from said cyclosiloxane precursor for a sufficient time to reduce the water and impurities in the cyclosiloxane precursor,
   (c) separating the cyclosiloxane precursor from the at least one adsorbent bed material, to produce a purified cyclosiloxane precursor, wherein the water content is less than 20 ppm;
   (d) vaporizing the purified cyclosiloxane precursor; and
   (e) delivering vapor of the purified cyclosiloxane precursor to said chemical vapor deposition reactor, wherein treatment of the cyclosiloxane precursor functions to prevent or minimize premature polymerization of the cyclosiloxane precursor in the chemical vapor deposition reactor and associated delivery lines and improves delivery reproducibility of the cyclosiloxane precursor.

2. The process according to claim 1, wherein said at least one impurity is acidic.

3. The process according to claim 1, wherein said at least one impurity is basic.

4. The process according to claim 1, wherein the cyclosiloxane precursor comprises the formula $[RR'Si—O]_n$, wherein each of R and R' is same or different and independently selected from the group consisting of hydrogen, hydroxyl, $C_1$–$C_8$ alkyl, $C_1$–$C_8$ alkoxy, $C_1$–$C_8$ alkene, $C_1$–$C_8$ alkyne, and $C_1$–$C_8$ carboxyl; and n is from 2 to 8.

5. The process according to claim 1, wherein the cyclosiloxane precursor is selected from the group consisting of polyhedral oligomeric silsesquioxanes (POSS), octamethylcyclotetrasiloxane (OMCTS), hexametbylcyclotetrasiloxane (HMCTS), tetramethylcyclotetrasiloxane (TMCTS), and mixtures thereof.

6. The process according to claim 1, wherein the cyclosiloxane precursor is 1,3,5,7-tetramethylcyclotetrasiloxane.

7. The process according to claim 1, wherein the at least one adsorbent bed material is selected from the group consisting of: silica gel, molecular sieves, aluminum oxide, carbon, calcium oxide, calcium chloride, sodium sulfate, magnesium perchlorate, phosphorus pentoxide, silacide, metals, and metal hydrides.

8. The process according to claim 7, wherein the at least one adsorbent bed material is calcium oxide.

9. The process according to claim 7, wherein the at least one adsorbent bed material is calcium hydride.

10. The process according to claim 7, wherein the cyclosiloxane precursor is further contacted with a second adsorbent bed material.

11. The process according to claim 7, wherein the purified cyclosiloxane precursor is removed from the at least one adsorbent bed material by distillation.

12. The process according to claim 7, wherein the purified cyclosiloxane precursor is removed from the at least one adsorbent bed material by decantation.

13. The process according to claim 7, wherein the purified cyclosiloxane precursor is removed from the at least one adsorbent bed material by pump.

14. The process according to claim 1, wherein the at least one adsorbent bed material comprises a combination of adsorbents.

15. A process for delivery of a cyclosiloxane precursor to a chemical vapor deposition reactor, the process comprising the steps of:
   (a) providing a cyclosiloxane precursor;
   (b) treating and contacting the cyclosiloxane precursor with at least one adsorbent bed material that has an affinity for water and at least one impurity selected from the group consisting of acidic and basic impurities from said cyclosiloxane precursor for a sufficient time to reduce the water and impurities in the cyclosiloxane precursor; and
   (c) separating the cyclosiloxane precursor from the at least one adsorbent bed material, to produce a purified cyclosiloxane precursor wherein said purified cyclosiloxane precursor comprises <0.001% of the at least one impurity.

16. A process for delivery of a cyclosiloxane precursor to a chemical vapor deposition reactor, the process comprising the steps of:
   (a) treating and contacting the cyclosiloxane precursor with at least one adsorbent bed material that has an affinity for water and at least one impurity selected from the group consisting of acidic and basic impurities from said cyclosiloxane precursor for a sufficient time to reduce the water and impurities in the cyclosiloxane precursor, and (b) separating the cyclosiloxane precursor from the at least one adsorbent bed material, to produce a purified cyclosiloxane precursor wherein said purified cyclosiloxane precursor comprises <0.00001% of the at least one impurity.

17. A process for delivery of a cyclosiloxane precursor to a chemical vapor deposition reactor, the process comprising the steps of: (a) treating and contacting the cyclosiloxane precursor with at least one adsorbent bed material that has an affinity for water and at least one impurity selected from the group consisting of acidic and basic impurities from said cyclosiloxane precursor for a sufficient time to reduce the water and impurities in the cyclosiloxane precursor; and (b) separating the cyclosiloxane precursor from the at least one adsorbent bed material, to produce a purified cyclosiloxane precursor wherein said purified cyclosiloxane precursor comprises less than 0.001% of water.

\* \* \* \* \*